United States Patent
Mortimer

(10) Patent No.: US 10,450,272 B2
(45) Date of Patent: Oct. 22, 2019

(54) HOMOGENEOUS PROCESS FOR HYDRODEHALOGENATING HALOGENATED HETEROARYL COMPOUNDS

(71) Applicant: JOHNSON MATTHEY PUBLIC LIMITED COMPANY, London (GB)

(72) Inventor: Danny Lee Mortimer, Hertfordshire (GB)

(73) Assignee: Johnson Matthey Public Limited Company, London, England (GB)

( * ) Notice: Subject to any disclaimer, the term of this patent is extended or adjusted under 35 U.S.C. 154(b) by 0 days.

(21) Appl. No.: 15/776,554

(22) PCT Filed: Nov. 16, 2016

(86) PCT No.: PCT/GB2016/053572
§ 371 (c)(1),
(2) Date: May 16, 2018

(87) PCT Pub. No.: WO2017/085476
PCT Pub. Date: May 26, 2017

(65) Prior Publication Data
US 2018/0334433 A1  Nov. 22, 2018

(30) Foreign Application Priority Data
Nov. 19, 2015  (GB) .................................. 1520379.7

(51) Int. Cl.
*C07D 213/61* (2006.01)
(52) U.S. Cl.
CPC .................................. *C07D 213/61* (2013.01)
(58) Field of Classification Search
CPC .................................................. C07D 213/61
See application file for complete search history.

(56) References Cited

FOREIGN PATENT DOCUMENTS

| | | |
|---|---|---|
| CN | 106518755 A1 | 3/2017 |
| EP | 2687510 A | 1/2014 |

OTHER PUBLICATIONS

Braun, Thomas et al., "Hydrodefluorination of Pentafluoropyridine at Rhodium Using Dihydrogen: Detection of Unusual Rhodium Hydrido Complexes," Dalton Transactions: The International Journal For Inorganic, Organometallic and Bioinorganic Chemistry, No. 34, Jan. 1, 2007, pp. 3820-3825.
Cucullu, M. (Grubbs) et al., "Catalytic Dehalogenation of Aryl Chlorides Mediated by Ruthenium(II) Phosphine Complexes," Organometallics, vol. 18, No. 7, 1999, pp. 1299-1304.
Zamostna Lada et al., "Catalytic Hydrofluorination of Fluoroaromatics With Silanes as Hydrogen Source at a Binuclear Rhodium Complex: Characterization of Key Intermediates," Journal of Fluorine Chemistry, vol. 155, May 29, 2013, pp. 132-142.
McKay, D. et al., "Mechanistic Study of Ru-NHC-Catalyzed Hydrodefluorination of Fluoropyridines: The Influence of the NHC on the Regioselectivity of C—F Activation and Chemoselectivity of C—F versus C—H Bond Cleavage," ACS Catalysis, vol. 5, Dec. 16, 2014, pp. 776-787.
Yus et al., "Metal-Mediated Reductive Hydrodehalogenation of Organic Halides," Chem. Rev., 2002, 102, 11, pp. 4009-4092.
Chelucci et al., "Synthetic Methods for the Hydrodehalogenation of Halogenated Heterocycles," Current Organic Chemistry, 2012, 16(24), 2921-2945.
Alper et al., "Rhodium(III) biphasic and phase-transfer-catalyzed hydrogenolysis of chloroarenes under exceptionally mild conditions," Organometallics, 1991, 10, 1620-1622.
PCT/GB2016/053572 International Search Report and Written Opinion dated Feb. 14, 2017.
GB1520379.7 Search Report under Section 17(5) dated Sep. 27, 2016.

*Primary Examiner* — Timothy R Rozof
(74) *Attorney, Agent, or Firm* — BakerHostetler

(57) ABSTRACT

The present invention provides a homogeneous process for hydrodehalogenating a halo-substituted $C_3$-$C_{20}$ heteroaryl starting material to form a non-halogenated $C_3$-$C_{20}$ heteroaryl product and/or a halo-substituted $C_3$-$C_{20}$ heteroaryl product, wherein the halo-substituted $C_3$-$C_{20}$ heteroaryl product has at least one less halogen substituents than the halo-substituted $C_3$-$C_{20}$ heteroaryl starting material, the process comprising the step of hydrogenating the halo-substituted $C_3$-$C_{20}$ heteroaryl starting material in the presence of a rhodium or ruthenium complex, molecular hydrogen, a base and a solvent, wherein the process is carried out in a monophasic solvent system and the molar ratio of base to each halogen substituent to be removed is at least 1:1.

26 Claims, No Drawings

HOMOGENEOUS PROCESS FOR HYDRODEHALOGENATING HALOGENATED HETEROARYL COMPOUNDS

CROSS-REFERENCE TO RELATED APPLICATIONS

This application is the National Stage of International Patent Application No. PCT/GB2016/053572, filed Nov. 16, 2016, which claims priority from Great Britain Patent Application No. 1520379.7, filed Nov. 19, 2015, the disclosures of each are incorporated herein by reference in their entireties for any and all purposes.

The present invention concerns a method for the homogeneous hydrodehalogenation of halo-substituted heteroaryl starting materials in the presence of rhodium or ruthenium complexes, wherein the process is carried out in a monophasic solvent system.

Hydrodehalogenation of halogenated heteroaromatics has been accomplished by catalytic hydrogenation employing a supported metal heterogeneous catalyst, transfer hydrogenation using Ni or Pd homogeneous catalysts or halogen-metal exchange reactions (Yus et al *M. Chem. Rev.* 2002, 102, 4009; Chelucci et al *Curr. Org. Chem.* 2012, 16, 2921). However, the handling of heterogeneous catalysts has the disadvantage of potential ignition on exposure to air, particularly when containing adsorbed hydrogen, whereas the halogen-metal exchange reactions require anhydrous conditions and low reaction temperatures.

Grubbs et al (*Organometallics* 1999, 18, 1299) reports the use of the complex $RuHCl(H_2)_2(PCy_3)_2$ as a homogeneous catalyst in dechlorination of 3-chloropyridine using sec-butyl alcohol as a transfer hydrogenation reagent.

Alper et al (*Organometallics* 1991, 10, 1620) reports the hydrogenolysis under 0.1 MPa $H_2$ of 5-chloro-1-ethyl-2-methylimidazole under biphasic conditions (aqueous NaOH in toluene) with the phase transfer catalyst benzyl triethylammonium chloride using $Rh(PCy_3)_2H_2Cl$ as a catalyst.

Braun et al (*Dalton Trans.* 2007, 3820-3825) describes the mono hydrodefluorination of pentafluoropyridine. The example describes the use of less than 1 molar equivalent of triethylamine to the fluorine atom to be removed. The conversion attained by Braun et al can be calculated 13% and the turnover frequency as $0.25\ h^{-1}$. The reaction is slow, incomplete and not commercially suitable. Braun et al neither discloses nor suggests the role of the base, nor why less than 1 molar equivalent was used, and nor that the catalytic turnover number (TON)/turnover frequency (TOF) is connected to the quantity of base utilised.

The regioselective hydrodehalogenation of halo-substituted heteroaryls has proven challenging in organic synthesis. EP2687510A describes the hydrodehalogenation of 2,3,6-trichloropyridine to 2,3-dichloropyridine using Pd/C heterogeneous catalyst, molecular hydrogen, triethylamine or pyridine as acid-binding agents and toluene as a solvent. However, this method uses a heterogeneous catalyst, which has the associated disadvantages described above.

SUMMARY OF THE INVENTION

The present invention provides an improved process for the homogeneous hydrodehalogenation of halogenated heteroaromatic compounds. The process is simple, economical, safe and does not require special equipment. In certain embodiments, the process may have environmental benefits by dehalogenating heteroaromatic compounds to form heteroaromatic compounds having fewer or no halogen atoms.

In one aspect, the invention provides a homogeneous process for hydrodehalogenating a halo-substituted $C_3$-$C_{20}$ heteroaryl starting material to form a non-halogenated $C_3$-$C_{20}$ heteroaryl product and/or a halo-substituted $C_3$-$C_{20}$ heteroaryl product, wherein the halo-substituted $C_3$-$C_{20}$ heteroaryl product has at least one less halogen substituent than the halo-substituted $C_3$-$C_{20}$ heteroaryl starting material, the process comprising the step of hydrogenating the halo-substituted $C_3$-$C_{20}$ heteroaryl starting material in the presence of a rhodium or ruthenium complex, molecular hydrogen, a base and a solvent, wherein the process is carried out in a monophasic solvent system and the molar ratio of base to each halogen substituent to be removed is at least 1:1.

Definitions

The point of attachment of a moiety or substituent is represented by "-". For example, —OH is attached through the oxygen atom.

"Alkyl" refers to a straight-chain or branched saturated hydrocarbon group. In certain embodiments, the alkyl group may have from 1-20 carbon atoms, in certain embodiments from 1-15 carbon atoms, in certain embodiments, 1-8 carbon atoms. The alkyl group may be unsubstituted. Alternatively, the alkyl group may be substituted. Unless otherwise specified, the alkyl group may be attached at any suitable carbon atom and, if substituted, may be substituted at any suitable atom. Typical alkyl groups include but are not limited to methyl, ethyl, n-propyl, iso-propyl, n-butyl, iso-butyl, sec-butyl, tert-butyl, n-pentyl, n-hexyl and the like.

"Aryl" refers to an aromatic carbocyclic group. The aryl group may have a single ring or multiple condensed rings. In certain embodiments, the aryl group can have from 6-20 carbon atoms, in certain embodiments from 6-15 carbon atoms, in certain embodiments, 6-12 carbon atoms. The aryl group may be unsubstituted. Alternatively, the aryl group may be substituted. Unless otherwise specified, the aryl group may be attached at any suitable carbon atom and, if substituted, may be substituted at any suitable atom. Examples of aryl groups include, but are not limited to, phenyl, naphthyl, anthracenyl and the like.

"Arylalkyl" refers to an optionally substituted group of the formula aryl-alkyl-, where aryl and alkyl are as defined above.

"Halo" or "halogen" refers to —F, —Cl, —Br and —I.

"Heteroalkyl" refers to a straight-chain or branched saturated hydrocarbon group wherein one or more carbon atoms are independently replaced with one or more heteroatoms (e.g. nitrogen, oxygen, phosphorus and/or sulfur atoms). In certain embodiments, the heteroalkyl group may have from 1-20 carbon atoms, in certain embodiments from 1-15 carbon atoms, in certain embodiments, 1-8 carbon atoms. The heteroalkyl group may be unsubstituted. Alternatively, the heteroalkyl group may substituted. Unless otherwise specified, the heteroalkyl group may be attached at any suitable atom and, if substituted, may be substituted at any suitable atom. Examples of heteroalkyl groups include but are not limited to ethers, thioethers, primary amines, secondary amines, tertiary amines and the like.

"Heterocycloalkyl" refers to a saturated cyclic hydrocarbon group wherein one or more carbon atoms are independently replaced with one or more heteroatoms (e.g. nitrogen, oxygen, phosphorus and/or sulfur atoms). In certain embodiments, the heterocycloalkyl group may have from 2-20 carbon atoms, in certain embodiments from 2-10 carbon atoms, in certain embodiments, 2-8 carbon atoms. The heterocycloalkyl group may be unsubstituted. Alternatively, the heterocycloalkyl group may be substituted. Unless otherwise specified, the heterocycloalkyl group may be attached at any suitable atom and, if substituted, may be substituted at any suitable atom. Examples of heterocycloalkyl groups include but are not limited to epoxide, morpholinyl, piperadinyl, piperazinyl, thiiranyl, pyrrolidinyl, pyrazolidinyl, imidazolidinyl, thiazolidinyl, thiomorpholinyl and the like.

"Heteroaryl" refers to an aromatic carbocyclic group wherein one or more carbon atoms are independently replaced with one or more heteroatoms (e.g. nitrogen, oxygen, phosphorus and/or sulfur atoms). In certain embodiments, the heteroaryl group may have from 3-20 carbon atoms, in certain embodiments from 3-15 carbon atoms, in certain embodiments, 3-8 carbon atoms. The heteroaryl group may be unsubstituted. Alternatively, the heteroaryl group may substituted. Unless otherwise specified, the heteroaryl group may be attached at any suitable atom and, if substituted, may be substituted at any suitable atom. Examples of heteroaryl groups include but are not limited to thienyl, furanyl, pyrrolyl, imidazolyl, pyrazolyl, thiazolyl, isothiazolyl, oxazolyl, isoxazolyl, triazolyl, thiadiazolyl, thiophenyl, oxadiazolyl, pyridinyl, pyrimidyl, benzoxazolyl, benzthiazolyl, benzimidazolyl, indolyl, quinolinyl and the like.

"Substituted" refers to a group in which one or more (e.g. 1, 2, 3, 4 or 5) hydrogen atoms are each independently replaced with substituents which may be the same or different. Examples of substituents include but are not limited to —C(halo)$_3$, —R$^a$, —O—R$^a$, —S—R$^a$, —NR$^a$R$^b$, —CN, —NO$_2$, —COOR$^a$, C(S)OR$^a$, —S(O)$_2$OH, —S(O)$_2$—R$^a$, —S(O)$_2$NR$^a$R$^b$, —O—S(O)—R$^a$ and —CON$^a$N$^b$, such as —R$^a$, —O—R$^a$, —NR$^a$R$^b$CN, —NO$_2$, —COOR$^a$ and —CON$^a$N$^b$; wherein R$^a$ and R$^b$ are independently selected from the groups consisting of H, alkyl, aryl, arylalkyl, heteroalkyl, heteroaryl, heteroaryl-alkyl-, or R$^a$ and R$^b$ together with the atom to which they are attached form a heterocycloalkyl group, and wherein R$^a$ and R$^b$ may be unsubstituted or further substituted as defined herein.

"Cp*" refers to 1,2,3,4,5-pentamethyl-cyclopentadienyl.

An "arene" is an unsubstituted or substituted benzene with one or more groups selected from straight or branched chain $C_{1-6}$ alkyl, straight or branched chain $C_{1-6}$ alkoxy, straight or branched chain $C_{1-6}$ carboalkoxy, —OH or NO$_2$.

A "monophasic solvent system" refers to a reaction system in which a solvent or a mixture of miscible solvents are used, and where the starting material, product and active catalytic species are soluble in the solvent.

By "non-coordinated anion ligand", we mean the anionic ligand is forced to the outer sphere of the metal centre. The anionic ligand, therefore, is dissociated from the metal centre. The non-coordinated anion ligand is selected from the group consisting of [BF$_4$]$^-$, [CF$_3$SO$_3$]$^-$, [PF$_6$]$^-$ and [SbF$_6$]$^-$.

DETAILED DESCRIPTION

Homogeneous hydrogenation reactions employing rhodium or ruthenium metal complexes are safer than reactions using supported metal catalysts. The purity of a reaction can be improved using homogeneous hydrogenation reactions as the purity of the reagents and complexes can be more easily controlled and fewer process parameters generally need to be considered in contrast to heterogeneous ones. For example, heterogeneous catalytic reactions may need to take into account the porosity of the catalyst, its particle size distribution, the age of the catalyst, the addition process, filtration, sheer stress and/or induction periods. These factors are ones which do not apply to homogeneous catalysts.

As mentioned above, in one aspect, the invention provides a homogeneous process for hydrodehalogenating a halo-substituted $C_3$-$C_{20}$ heteroaryl starting material to form a non-halogenated $C_3$-$C_{20}$ heteroaryl product and/or a halo-substituted $C_3$-$C_{20}$ heteroaryl product, wherein the halo-substituted $C_3$-$C_{20}$ heteroaryl product has at least one less halogen substituent than the halo-substituted $C_3$-$C_{20}$ heteroaryl starting material, the process comprising the step of hydrogenating the halo-substituted $C_3$-$C_{20}$ heteroaryl starting material in the presence of a rhodium or ruthenium complex, molecular hydrogen, a base and a solvent, wherein the process is carried out in a monophasic solvent system and the molar ratio of base to each halogen substituent to be removed is at least 1:1.

In one embodiment, the halo-substituted $C_3$-$C_{20}$ heteroaryl starting material has a number of halogen substituents which is ≥2 and up to the limitations imposed by stability and the rules of valence, for example 2, 3, 4 or 5, such as 2 or 3 halogen substituents.

In another embodiment, the halo-substituted $C_3$-$C_{20}$ heteroaryl starting material has a number of halogen substituents which is >2 and up to the limitations imposed by stability and the rules of valence.

In yet another embodiment, the halo-substituted $C_3$-$C_{20}$ heteroaryl starting material has 2 halogen substituents, and the $C_3$-$C_{20}$ heteroaryl product has one or no halogen substituents.

In one embodiment, the halo-substituted $C_3$-$C_{20}$ heteroaryl starting material is a halo-substituted $C_3$-$C_{15}$ heteroaryl starting material. In this instance, the starting material may form on hydrogenation a non-halogenated $C_3$-$C_{15}$ heteroaryl product and at least one halo-substituted $C_3$-$C_{15}$ heteroaryl product.

The halo-substituted $C_3$-$C_{15}$ heteroaryl starting material may be a halo-substituted $C_3$-$C_{10}$ heteroaryl starting material. In this instance, the starting material may form on hydrogenation a non-halogenated $C_3$-$C_{10}$ heteroaryl product and at least one halo-substituted $C_3$-$C_{10}$ heteroaryl product.

The halo-substituted $C_3$-$C_{10}$ heteroaryl starting material may be a halo-substituted $C_3$-$C_5$ heteroaryl starting material. In this instance, the starting material may form on hydrogenation a non-halogenated $C_3$-$C_5$ heteroaryl product and at least one halo-substituted $C_3$-$C_5$ heteroaryl product.

In another embodiment, the halo-substituted $C_3$-$C_{20}$ heteroaryl starting material is a halo-substituted $C_3$-$C_{20}$ nitrogen-containing heteroaryl. In this instance, the product is a halo-substituted $C_3$-$C_{20}$ nitrogen-containing heteroaryl comprising at least one less halogen substituent than the halo-substituted starting material.

In another embodiment, the halogen in the halo-substituted $C_3$-$C_{20}$ heteroaryl starting material and product may be independently selected from fluorine (—F), chlorine (—Cl), bromine (—Br) or iodine (—I), for example, chlorine, bromine and iodine.

In one embodiment, the halogens are the same.

In another embodiment, the halogens are different.

In one preferred embodiment, the halogens are the same and are chlorine atoms.

In another embodiment, the halo-substituted $C_3$-$C_{20}$ heteroaryl starting material and halo-substituted $C_3$-$C_{20}$ heteroaryl product are chloro-substituted $C_3$-$C_{20}$ heteroaryls.

In one embodiment, the starting material is a trichloro-pyridine and the product is a dichloro-pyridine. When the starting material is 2,3,6-trichloro-pyridine, the product may be 2,3-dichloro-pyridine. 2,3-Dichloro-pyridine is a useful intermediate in the synthesis of crop protection insecticides, such as chlorantraniliprole and cyantraniliprole.

The hydrodehalogenation process may be regioselective. Without wishing to be bound by theory, in metal-catalyzed hydrodehalogenation reactions the selectivity when the halogens are the same is determined by electronic and steric factors within the starting material. The process of the present invention, therefore, may allow the regioselective hydrodehalogenation of halogen substituents in non-adjacent positions in the starting material.

Without wishing to be bound by theory, the base regenerates the active catalytic species and thereby drives the reaction towards product formation.

Any suitable base may be used provided that it does not adversely react with the starting material or product.

The base may be an inorganic base such as an alkali metal hydroxide, alkali metal carbonate, alkali-earth metal oxide.

Suitable alkali metal hydroxides include but are not limited to NaOH, KOH, preferably NaOH.

Suitable alkali metal carbonates include but are not limited to lithium carbonate, sodium carbonate or potassium carbonate, preferably sodium carbonate.

Suitable metal oxides include but are not limited to MgO.

The base may be an organic base, such as an aliphatic tertiary amine. Suitable aliphatic tertiary amines include but are not limited to triethyl amine, triisopropyl amine, N,N-diisopropylethylamine, preferably triethyl amine.

Any suitable amount of base may be used provided that the molar ratio of base to each halogen to be removed in the halo-substituted $C_3$-$C_{20}$ heteroaryl starting material is at least 1:1. A stoichiometric number of moles of base to starting material may be used when the starting material itself contains basic functional groups. In this instance, the starting material may contribute to the basicity of the reaction mixture. Without wishing to be bound by theory, it is believed that the process of the present invention proceeds at a suitable rate in basic conditions as suitable turnover numbers (TONs) or turnover frequencies (TOFs) can be achieved.

If desired, the molar quantity of base may be in excess to the molar quantity of halogen (or halogens) to be removed. The amount of base may be calculated to provide a molar excess of between about 0.1 to about 1.0 molar equivalents over the amount required for the stoichiometric reaction (such as about 0.5 to about 0.75 molar equivalents in excess). For example, when one halogen atom is to be removed from the halo-substituted $C_3$-$C_{20}$ heteroaryl starting material, about 1.1 to about 2.0 molar equivalents with respect to the $C_3$-$C_{20}$ heteroaryl starting material may be used, preferably about 1.75 equivalents. An excess of base therefore may be desirable to drive the reaction to completion (i.e. achieve full conversion) more quickly and may allow for lower catalyst loadings. If the the halo-substituted $C_3$-$C_{20}$ heteroaryl starting material contains acidic functional groups, a greater excess of base may be required to drive the reaction to completion.

The solvent may be selected from the group consisting of alcohols and aromatic solvents.

Suitable alcohols have boiling points at atmospheric pressure (i.e. $1.0135 \times 10^5$ Pa) below 160° C. Examples include but are not limited to methanol, ethanol, propanol isomers (e.g. 1-propanol or 2-propanol), butanol isomers (e.g. 1-butanol, 2-butanol), pentanol isomers (e.g. 1-propanol, 2-pentanol, 3-pentanol, neopentyl alcohol, tert-pentyl alcohol, iso-pentyl alcohol or cyclopropanol) and hexanol isomers (e.g. 1-hexanol, 2-hexanol, 3-hexanol or cyclohexanol). In one embodiment, the alcohol may be selected from the group consisting of 2-propanol (IPA), ethanol and methanol.

Suitable aromatic solvents are selected from the group consisting of benzene, toluene and xylene, preferably toluene.

The concentration of the starting material in the solvent is preferably about 1 g/L to about 500 g/L, for example, about 50 g/L to about 250 gl/L, such as about 100 g/L to about 150 g/L, such as about 111 g/L.

In one embodiment, the homogeneous rhodium complex is a rhodium(I) complex or a rhodium(III) complex.

In another embodiment, the homogeneous rhodium(I) complex is selected from the group consisting of Rh(monophosphine)$_3$X, Rh(monophosphine)$_2$(CO)X, Rh(monophosphine)$_3$(CO)H, Rh(monophosphine)$_4$H, [Rh(CO)$_2$X]$_2$, [Rh(olefin)$_m$X]$_2$, Rh(olefin)$_m$Cp*, [Rh(olefin)$_m$(phosphine)$_n$]Y, and complexes generated in situ from [Rh(olefin)$_m$X]$_2$ and phosphine, wherein, X is a halogen, Y is a non-coordinated anionic ligand, preferably [BF$_4$]$^-$, [CF$_3$SO$_3$]$^-$, [PF$_6$]$^-$ or [SbF$_6$]$^-$, the phosphine is a monophosphine or a diphosphine, m is 1 or 2, n is 1 or 2, and wherein, when m=1, the olefin is a diolefin, when m=2, the olefin is a mono-olefin, when n=1, the phosphine is a bidentate phosphine, and when n=2, the phosphine is a monophosphine.

The monophosphine may be a triaryl phosphine, a trialkyl phosphine, phosphite esters, mixed phosphites/phosphanes, or a mixture thereof, such as a triaryl phosphine or a trialkyl phosphine or a mixture thereof.

Suitable triaryl phosphines include but are not limited to PPh$_3$, P(tol)$_3$ (e.g. o-tol, m-tol and p-tol), preferably P(o-tol)$_3$ or PPh$_3$.

Suitable trialkyl phosphines include but are not limited to PCy$_3$, PPr$_3$ (eg n- or i-Pr, preferably i-Pr), PBu$_3$ (eg n-, i- or t-Bu, preferably P(t-Bu)$_3$).

Suitable diphosphines include but are not limited to 1,2-bis(di-phenyl phosphino)butane, 1,1'-bis(di-phenyl phosphino)ferrocene, 1,1'-bis(di-cyclohexyl phosphino)ferrocene, 1,1'-bis(di-tertbutyl phosphino)ferrocene, 2,2'-bis(diphenylphosphino)-1,1'-binaphthyl.

Suitable phosphite esters include but are not limited to P(O-alkyl)$_3$ (such as P(OMe)$_3$) or P(O-aryl)$_3$ (e.g. P(OPh)$_3$).

Suitable mixed phosphite/phosphanes include but are not limited to P(O-alkyl)$_2$(aryl) (such as P(OMe)$_2$Ph), P(O-alkyl)(aryl)$_2$ (such as P(OMe)Ph$_2$), P(O-aryl)$_2$(alkyl) (e.g. P(OPh)$_2$Me) or P(O-aryl)(alkyl)$_2$ (e.g. P(OPh)Me$_2$).

The reaction of [Rh(olefin)$_m$X]$_2$ and phosphine may yield a mixture of complexes where no individual complex can be isolated and characterised. Accordingly, the homogeneous rhodium (I) complex may comprise complexes generated in situ from [Rh(olefin)$_m$X]$_2$ and phosphine.

The diolefin may be an acyclic diolefin, such as 1,5-hexadiene, or a cyclic diolefin, preferably 2,5-norbornadiene (NBD) or 1,5-cyclooctadiene (COD).

Alternatively the cyclic diolefin can be replaced by either two molecules of an olefin such as ethylene or two molecules of a $C_{5-10}$ cycloalkene, such as cyclooctene.

In one embodiment, X is Cl.

Y is a non-coordinated anionic ligand. In one embodiment, Y may be selected from the group consisting of [BF$_4$]$^-$, [CF$_3$SO$_3$]$^-$, [PF$_6$]$^-$ or [SbF$_6$]$^-$.

The molar ratio of rhodium complexes to starting material is preferably about 1:2500 to about 1:30, for example, about 1:1000 to 1:40, such as about 1:500 to 1:50, such as about 1:58.

Suitable rhodium(I) complexes include but are not limited to Rh(PPh$_3$)$_3$Cl, Rh(PPh$_3$)$_3$Br, Rh(PPh$_3$)$_2$(CO)Cl, Rh(PPh$_3$)$_3$(CO)H, Rh(PPh$_3$)$_4$H, [Rh(CO)$_2$Cl]$_2$, [Rh(COD)Cl]$_2$, [Rh(NBD)Cl]$_2$, [Rh(1,5-hexadiene)Cl]$_2$, [Rh(ethylene)$_2$Cl]$_2$, [Rh(cyclooctene)$_2$Cl]$_2$, Rh(COD)Cp*, [Rh(dcypf)(COD)]BF$_4$, [Rh(dippf)(COD)]BF$_4$, [Rh(dppf)(COD)]BF$_4$, [Rh(dtbpf)(COD)]BF$_4$, [Rh(dppb)(COD)]BF$_4$, [Rh(dcypf)(NBD)]BF$_4$, [Rh(dippf)(NBD)]BF$_4$, [Rh(dppf)(NBD)]BF$_4$, [Rh(dtbpf)(NBD)]BF$_4$, [Rh(dppb)(NBD)]BF$_4$, [Rh((R)-BINAP)(COD)]BF$_4$, wherein dcypf=1,1'-bis(di-cyclohexyl phosphino)ferrocene, dippf=1,1'-bis(di-isopropyl phosphino)ferrocene, dppf=1,1'-bis(di-phenyl phosphino)ferrocene, dtbpf=1,1'-bis(di-tertbutyl phosphino)ferrocene, dppb=1,2-bis(di-phenyl phosphino)butane.

The rhodium(I) complexes may be pre-formed or generated in situ, such as by adding phosphines to [Rh(COD)Cl]$_2$, [Rh(NBD)Cl]$_2$, [Rh(1,5-hexadiene)Cl]$_2$, [Rh(ethylene)$_2$Cl]$_2$, [Rh(cyclooctene)$_2$Cl]$_2$ in the reaction mixture.

In another embodiment, the rhodium(III) complex is selected from the group consisting of Rh(monophosphine)$_2$X$_p$H$_q$ and [Rh(Cp*)X$_2$]$_2$,
wherein,
X is a halogen,
p is 1 or 2
q is 2 or 1, and
p+q is 3.

X and the monophosphine are as generally described above.

Suitable rhodium(III) complexes include but are not limited to Rh(PiPr$_3$)$_2$H$_2$Cl, Rh(PiPr$_3$)$_2$HCl$_2$, Rh(PCy$_3$)$_2$HCl$_2$ and [RhCp*C$_2$]$_2$.

Preferred Rh complexes are Rh(PPh$_3$)$_3$Cl and [RhCp*Cl$_2$]$_2$.

In another embodiment, the homogeneous ruthenium complex is selected from the group consisting of Ru(monophosphine)$_3$X$_2$, Ru(monophosphine)$_3$HX, Ru(monophosphine)$_2$(CO)$_2$X$_2$, Ru(monophosphine)$_3$(CO)X$_r$H$_s$, [Ru(Cp*)X$_2$] polymer, Ru(Cp*)(monophosphine)$_2$X, [Ru(arene)X$_2$]$_2$, Ru(monophosphine)(arene)X$_2$, [Ru(olefin)$_t$X$_2$] polymer, Ru(olefin)$_t$(Cp*)X, and complexes generated in situ from [Ru(olefin)$_t$X$_2$] polymer and optionally phosphine,
wherein:
X is a halogen,
the phosphine is a monophosphine or a diphosphine,
t is 1 or 2,
r is 0 or 1
s is 2 or 1, and
r+s is 2,
and wherein,
when t=1, the olefin is a diolefin,
when t=2, the olefin is a mono-olefin.

The phosphine may be a triaryl phosphine, a trialkyl phosphine, phosphite esters, mixed phosphites/phosphanes, or a mixture thereof, such as a triaryl phosphine or a trialkyl phosphine or a mixture thereof.

Suitable triaryl phosphines include but are not limited to PPh$_3$, P(tol)$_3$ (e.g. o-tol, m-tol and p-tol), preferably P(o-tol)$_3$) or PPh$_3$.

Suitable trialkyl phosphines include but are not limited to PCy$_3$, PPr$_3$ (e.g. n- or i-Pr, preferably i-Pr), PBu$_3$ (eg n-, i- or t-Bu, preferably P(t-Bu)$_3$).

Suitable phosphite esters include but are not limited to P(O-alkyl)$_3$ (such as P(OMe)$_3$) or P(O-aryl)$_3$ (e.g. P(OPh)$_3$).

Suitable mixed phosphite/phosphanes include but are not limited to P(O-alkyl)$_2$(aryl) (such as P(OMe)$_2$Ph), P(O-alkyl)(aryl)$_2$ (such as P(OMe)Ph$_2$), P(O-aryl)$_2$(alkyl) (e.g. P(OPh)$_2$Me) or P(O-aryl)(alkyl)$_2$ (e.g. P(OPh)Me$_2$).

Suitable diphosphines include but are not limited to 1,2-bis(di-phenyl phosphino)butane (dppb), 1,1'-bis(di-phenyl phosphino)ferrocene (dippf), 1,1'-bis(di-cyclohexyl phosphino)ferrocene (dcypf), 1,1'-bis(di-tertbutyl phosphino)ferrocene (dtbpf), 2,2'-bis(diphenylphosphino)-1,1'-binaphthyl.

Suitable arenes include but are not limited to benzene, cymene, toluene, xylene, trimethylbenzene, hexamethylbenzene, ethylbenzene, t-butylbenzene, cumene (isopropylbenzene), 1-phenylindenyl, anisole (methoxybenzene), methylanisole, chlorobenzene, dichlorobenzene, trichlorobenzene, bromobenzene, fluorobenzene, methylbenzoate and methyl methyl benzoate (e.g. methyl 2-methylbenzoate). Preferably, the arene is benzene, p-cymene or mesitylene (1,3,5-trimethylbenzene).

X is a halogen. In one embodiment, X is Cl.

The reaction of a [Ru(olefin)$_t$X$_2$] polymer and phosphine may yield a mixture of complexes where no individual complex can be isolated and characterised. Accordingly, the homogeneous ruthenium complex may comprise complexes generated in situ from [Ru(olefin)$_t$X$_2$] polymer and phosphine.

The diolefin may be a acyclic diolefin, such as 1,5-hexadiene, or a cyclic diolefin, preferably 2,5-norbornadiene (NBD) or 1,5-cyclooctadiene (COD).

Alternatively the cyclic diolefin can be replaced by either two molecules of an olefin such as ethylene or two molecules of a C$_{5-10}$ cycloalkene, such as cyclooctene.

The molar ratio of ruthenium complexes to starting material is preferably about 1:2500 to about 1:30, for example, about 1:1000 to 1:40, such as about 1:500 to 1:50, such as about 1:58.

Suitable Ru complexes include but are not limited to Ru(PPh$_3$)$_3$Cl$_2$, Ru(PPh$_3$)$_3$Br$_2$, Ru(PPh$_3$)$_3$HCl, Ru(PPh$_3$)$_2$(CO)$_2$Cl$_2$, Ru(PiPr$_3$)$_3$(CO)ClH, Ru(PPh$_3$)$_3$(CO)H$_2$, [RuCl$_2$Cp*] polymer, RuCl(PPh$_3$)$_2$Cp*, [RuCl$_2$(p-cymene)]$_2$, [RuI$_2$(p-cymene)]$_2$, [RuCl$_2$(benzene)]$_2$, [RuCl$_2$(mesitylene)]$_2$, RuCl$_2$(p-cymene)(PPh$_3$), RuCl$_2$(p-cymene)(PCy$_3$), Ru(COD)ClCp*, [Ru(COD)Cl$_2$] polymer in the presence or absence of added phosphine.

The reactants may be added in any suitable order, but in one embodiment of the invention, the complex and the base is added to the reactor, followed by a solution of the starting material in solvent. In another embodiment, the starting material, complex and solvent are added to the reactor, followed by the base. In yet another embodiment, the complex is added to the reactor, followed by a solution of the starting material in solvent and the base. The reactor may be purged with nitrogen (e.g. 3 times) and hydrogen (e.g. 3 times) with stirring, then hydrogenated with hydrogen gas.

The process of the invention may be carried out at one or more pressures in the range of about 0.2 to about 3 MPa, preferably about 0.3 to about 1 MPa.

It is envisaged that the hydrodehalogenation may also be carried out using deuterium or tritium.

The process of the invention may be carried out at one or more temperatures in the range of about 30° C. to the boiling point of the solvent, preferably about 40° C. to about 100° C., for example, about 60° C. to about 90° C.

The reaction may be carried out for a period of from several minutes to about 24 hours but is usually complete within about 3 hours.

On completion the product is separated from the reaction mixture by any appropriate method which is dependent upon the physical form of the product. For example, the product may be extracted from the reaction mixture by combining the reaction mixture with an organic solvent (such as ethyl acetate) and water, separating, drying the organic layer and removing solvent under reduced pressure.

Other Preferences

Each and every compatible combination of the embodiments described above is explicitly disclosed herein, as if each and every combination was individually and explicitly recited.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

The invention will be further described with reference to the following non-limiting Examples.

EXAMPLES

Example 1

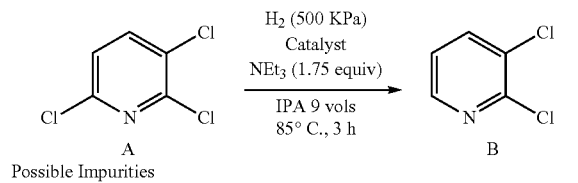

A
Possible Impurities

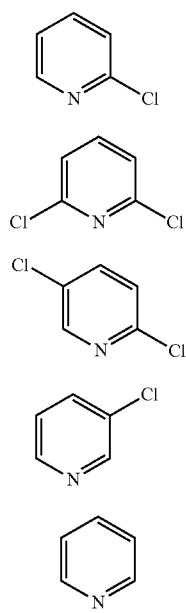

Non-Optimised Reaction Conditions are as Follows:

Complex (1.71 mol %) and 3 mL of stock solution (made from 3.333 g TCP A in IPA 30 mL) are added to each reactor, followed by NEt$_3$ (446 μL). The reactors are purged with nitrogen (3 times) and hydrogen (3 times) then hydrogenated at 0.5 MPa and 85° C. for 180 min in a Biotage Endeavor. 40 μL aliquot of each reaction mixture is added to 1 mL MeCN and analysed by normal HPLC method. HPLC areas are converted to concentration (μmol/mL) from the gradients equations in the multipoint external standard.

TABLE 1

HPLC converted concentrations various catalysts (1.71 mol %); NEt$_3$ (1.75 equiv), IPA (9 vol.), 85° C., 180 mins, 0.5 MPa H$_2$.[a]

| entry | catalyst | Concentration μmol/mL | | | | | | DCP B selec- tivity (%) |
| | | Pyr E | MCP D | MCP C | DCP B | DCP F | TCP A | |
|---|---|---|---|---|---|---|---|---|
| 1 | Rh(PPh$_3$)$_3$Cl | 0.35 | 0.53 | 0.53 | 33.35 | 0 | 0 | 95.96 |
| 2 | [RhCp*Cl$_2$]$_2$ | 1.36 | 9.00 | 0.60 | 10.61 | 4.01 | 10.40 | 40.96 |
| 3 | [RuCl$_2$(COD)] polymer | 0.20 | 0.14 | 0.92 | 5.20 | 0.57 | 15.81 | 73.91 |
| 4 | Ru(PPh$_3$)$_3$Cl$_2$ | 3.10 | 1.14 | 0.64 | 1.78 | 2.64 | 35.63 | 18.58 |

[a]HPLC method: Flow rate: 1 mL/min, Column Temperature: 20° C., Column C18 Amide 100A 250 × 4.6 mm, 10 microL injection, UV 210 nm. Isochratic: H$_2$O:MeCN (50:50) (0.1% H$_3$PO$_4$). 15 min UV analysis.

Several rhodium and ruthenium complexes are investigated as catalysts in the hydrodehalogenation of 2,3,6-trichloro-pyridine, under hydrogenation conditions using H$_2$ gas at 0.5 MPa, in the presence of NEt$_3$ (1.75 equiv), in 2-propanol (IPA), at 85° C., over 3 hours. The conversion is higher when rhodium catalysts are employed, the reaction being complete when using Rh(PPh$_3$)$_3$Cl. The selectivity towards 2,3-dichloro-pyridine is also highest when this catalyst is used.

Example 2

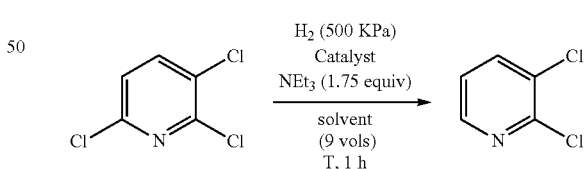

TCP A (333 mg), complex (1.71 mol %) and solvent (3 mL) are added to each reactor, followed by NEt$_3$ (446 microL). The reactor is purged with nitrogen (3 times) and hydrogen (3 times) then hydrogenated at 5 bar and various reactor temperatures for 60 mins in a Biotage Endeavor. 40 μL aliquot of each reaction mixture is added to 1 mL MeCN and analysed by normal HPLC method.

HPLC areas are converted to concentration (μmol/mL) from the gradients equations in the multipoint external standard.

TABLE 2

HPLC converted concentrations Rh (PPh$_3$)$_3$Cl (1.71 mol %); NEt$_3$ (1.75 eq.),
various solvents (9 vol.), varying temperature, 60 mins, 0.5 MPa H$_2$.[a]

| | | | Concentration μmol/mL | | | | | | DCP B |
|---|---|---|---|---|---|---|---|---|---|
| Entry | Solvent | T/° C. | Pyr E | MCP D | MCP C | DCP B | DCP F | TCP A | selectivity % |
| 1 | IPA | 65 | 1.51 | 0.72 | 1.95 | 43.84 | 1.18 | 49.89 | 89.11 |
| 2 | IPA | 70 | 1.59 | 0.78 | 1.25 | 59.13 | 1.25 | 25.53 | 92.39 |
| 3 | IPA | 75 | 1.01 | 0.89 | 1.11 | 70.99 | 1.13 | 5.72 | 94.48 |
| 4 | IPA | 80 | 1.75 | 0.69 | 2.05 | 75.54 | 0.56 | 0.16 | 93.73 |
| 5 | IPA | 85 | 0.43 | 1.36 | 8.66 | 80.88 | 0 | 0 | 88.56 |
| 6 | EtOH | 65 | 1.67 | 0.66 | 0.64 | 54.99 | 1.59 | 30.9 | 92.36 |
| 7 | EtOH | 80 | 2.30 | 1.56 | 2.00 | 84.94 | 0 | 0.05 | 93.55 |
| 8 | MeOH | 65 | 2.02 | 0.83 | 0.63 | 53.61 | 2.13 | 34.23 | 90.53 |

[a]HPLC method: Flow rate: 1 mL/min, Column Temperature: 20° C., Column C18 Amide 100A 250 × 4.6 mm, 10 microL injection, UV 210 nm. Isochratic: H$_2$O:MeCN (50:50) (0.1% H$_3$PO$_4$). 15 min UV analysis.

Several hydrogenation experiments using H$_2$ gas (0.5 MPa) and NEt$_3$ (1.75 equiv) are carried out using Rh(PPh$_3$)$_3$Cl (1.71 mol %) as a complex, in various solvents and at different temperatures, over 1 h. Conversion increases with the temperature (entries 1-5 and 6-7). When the reaction is carried out at the same temperature of 65° C., the conversion is highest in ethanol (entries 1, 6 and 8).

The experiment in entry 5 is subjected to a work-up. Combining the reaction mixture with EtOAc and H$_2$O, separating, drying the organic layer and removing solvent under reduced pressure gives crude material 238.5 mg, (88% yield of pure DCP B). $^1$H NMR shows excellent selectivity showing only DCP B and residual catalyst complex.

The invention claimed is:

1. A homogeneous process for hydrodehalogenating a halo-substituted C$_3$-C$_{20}$ heteroaryl starting material to form a non-halogenated C$_3$-C$_{20}$ heteroaryl product and/or a halo-substituted C$_3$-C$_{20}$ heteroaryl product, wherein the halo-substituted C$_3$-C$_{20}$ heteroaryl product has at least one less halogen substituent than the halo-substituted C$_3$-C$_{20}$ heteroaryl starting material, the process comprising the step of:
hydrogenating the halo-substituted C$_3$-C$_{20}$ heteroaryl starting material in the presence of a rhodium or ruthenium complex, molecular hydrogen, a base and a solvent, wherein the process is carried out in a monophasic solvent system and the base is present in a molar excess of between 0.1 to 1.0 molar equivalents over an amount required for the stoichiometric reaction to remove each halogen substituent.

2. The process of claim 1, wherein the halo-substituted C$_3$-C$_{20}$ heteroaryl starting material has a number of halogen substituents which is ≥2 and up to the limitations imposed by the rules of valence.

3. The process of claim 1, wherein the halo-substituted C$_3$-C$_{20}$ heteroaryl starting material is a halo-substituted C$_3$-C$_{15}$ heteroaryl starting material.

4. The process of claim 1, wherein the halo-substituted C$_3$-C$_{20}$ heteroaryl starting material is a halo-substituted C$_3$-C$_{20}$ nitrogen-containing heteroaryl starting material.

5. The process of claim 1, wherein the halo-substituted C$_3$-C$_{20}$ heteroaryl starting material is a chloro-substituted C$_3$-C$_{20}$ heteroaryl starting material.

6. The process of claim 1, wherein the halo-substituted C$_3$-C$_{20}$ heteroaryl starting material is trichloro-pyridine.

7. The process of claim 1, wherein the halo-substituted C$_3$-C$_{20}$ heteroaryl product is a halo-substituted C$_3$-C$_{20}$ nitrogen-containing heteroaryl product.

8. The process of claim 1, wherein the halo-substituted C$_3$-C$_{20}$ heteroaryl product is a chloro-substituted C$_3$-C$_{20}$ heteroaryl product.

9. The process of claim 1, wherein the halo-substituted C$_3$-C$_{20}$ heteroaryl product is a halo-substituted C$_3$-C$_{20}$ nitrogen-containing heteroaryl product.

10. The process of claim 1, wherein the halo-substituted C$_3$-C$_{20}$ heteroaryl product is dichloro-pyridine.

11. The process of claim 1, wherein the base is an inorganic base or an organic base.

12. The process of claim 1, wherein the base is present in a molar ratio of about 1.1:1 to about 2:1 to each halogen substituent to be removed.

13. The process of claim 12, wherein the base is present in a molar ratio of about 1.5:1 to about 1.75:1 to each halogen substituent to be removed.

14. The process of claim 1, wherein the solvent is an alcohol or aromatic solvent.

15. The process of claim 14, wherein the alcohol has a boiling point at atmospheric pressure below 160° C.

16. The process of claim 14, wherein the aromatic solvent is benzene, toluene or xylene.

17. The process of claim 1, wherein the molecular hydrogen is molecular deuterium or molecular tritium.

18. The process of claim 1, wherein the rhodium complex is a rhodium(I) complex or a rhodium(III) complex.

19. The process of claim 18, wherein the rhodium(I) complex is Rh(monophosphine)$_3$X, Rh(monophosphine)$_2$(CO)X, Rh(monophosphine)$_3$(CO)H, Rh(monophosphine)$_4$H, [Rh(CO)$_2$X]$_2$, [Rh(olefin)$_m$X]$_2$, Rh(olefin)$_m$Cp*, [Rh(olefin)$_m$(phosphine)$_n$]Y, or a complex generated in situ from [Rh(olefin)$_m$X]$_2$ and phosphine, wherein:
Cp* is 1,2,3,4,5-pentamethyl-cyclopentadienyl;
X is a halogen,
Y is a non-coordinated anionic ligand,
the phosphine is a monophosphine or a diphosphine,
m is 1 or 2,
n is 1 or 2, and wherein:
when m=1, the olefin is a diolefin,
when m=2, the olefin is a mono-olefin,
when n=1, the phosphine is a bidentate phosphine, and
when n=2, the phosphine is a monophosphine.

20. The process of claim 18, wherein the rhodium(III) complex is Rh(monophosphine)$_2$X$_p$H$_q$ or [Rh(Cp*)X$_2$]$_2$, wherein:
X is a halogen,
p is 1 or 2,
q is 2 or 1, and
p+q is 3.

21. The process of claim 1, wherein the ruthenium complex is Ru(monophosphine)$_3$X$_2$, Ru(monophosphine)$_3$HX, Ru(monophosphine)$_2$(CO)$_2$X$_2$, Ru(monophosphine)$_3$(CO)X$_r$H$_s$, [Ru(Cp*)X$_2$] polymer, Ru(Cp*)(monophosphine)$_2$X, [Ru(arene)X$_2$]$_2$, Ru(monophosphine)(arene)X$_2$, [Ru(olefin)$_r$X$_2$] polymer, Ru(olefin)t(Cp*)X, or a complex generated in situ from [Ru(olefin)$_r$X$_2$] polymer and phosphine, wherein:
X is a halogen,
the phosphine is a monophosphine or a diphosphine,
t is 1 or 2,
r is 0 or 1,
s is 2 or 1, and
r+s is 2, and
wherein:
when t=1, the olefin is a diolefin,
when t=2, the olefin is a mono-olefin.

22. The process of claim 19, wherein the mono-olefin is ethylene or cyclooctene.

23. The process of claim 21, wherein the diolefin is 1,5-hexadiene, cyclooctadiene or norbornadiene.

24. The process of claim 19, wherein the diolefin is 1,5-hexadiene, cyclooctadiene or norbornadiene.

25. The process of claim 21, wherein the diolefin is 1,5-hexadiene, cyclooctadiene or norbornadiene.

26. The process of claim 16, wherein Y is [BF$_4$]$^-$, [CF$_3$SO$_3$]$^-$, [PF$_6$]$^-$ or [SbF$_6$]$^-$.

\* \* \* \* \*